(12) United States Patent
Roche et al.

(10) Patent No.: US 9,545,464 B2
(45) Date of Patent: Jan. 17, 2017

(54) SYRINGE WITH RATCHETING OPERATING ROD AND LOCKABLE PLUNGER HEAD

(71) Applicant: STEMCIS, Sainte-clotilde (FR)

(72) Inventors: Regis Roche, La Montagne/Reunion (FR); Franck Festy, La Montagne/Reunion (FR)

(73) Assignee: STEMCIS, Sainte-Clotilde (FR)

( * ) Notice: Subject to any disclaimer, the term of this patent is extended or adjusted under 35 U.S.C. 154(b) by 150 days.

(21) Appl. No.: 14/383,575

(22) PCT Filed: Mar. 7, 2013

(86) PCT No.: PCT/FR2013/050483
§ 371 (c)(1),
(2) Date: Sep. 8, 2014

(87) PCT Pub. No.: WO2013/132192
PCT Pub. Date: Sep. 12, 2013

(65) Prior Publication Data
US 2015/0105754 A1    Apr. 16, 2015

(30) Foreign Application Priority Data
Mar. 8, 2012 (FR) ...................... 12 52122

(51) Int. Cl.
*A61M 1/00* (2006.01)
*A61M 5/315* (2006.01)

(52) U.S. Cl.
CPC ........... *A61M 1/007* (2014.02); *A61M 1/0009* (2013.01); *A61M 5/31505* (2013.01);
(Continued)

(58) Field of Classification Search
CPC .............. A61M 1/007; A61M 5/31505; A61M 2005/31508; A61M 2202/0014; A61M 2202/08; A61M 2205/3341; A61M 5/315; A61M 5/5013; A61M 5/502
See application file for complete search history.

(56) References Cited

U.S. PATENT DOCUMENTS 3,747,812 A * 7/1973 Karman ............... A61B 5/1405
222/387
3,811,441 A * 5/1974 Sarnoff ................... A61M 5/24
604/201

(Continued)

FOREIGN PATENT DOCUMENTS

GB        958 636       5/1964
GB      1 225 495       3/1971

OTHER PUBLICATIONS

International Search Report dated Jun. 28, 2013, corresponding to PCT/FR2013/050483.

*Primary Examiner* — Nathan R Price
*Assistant Examiner* — John Doubrava
(74) *Attorney, Agent, or Firm* — Young & Thompson

(57) ABSTRACT

A syringe for medical applications includes a syringe body having an inner wall, a first stop, located along the inner wall, to leave at least one first blank surface on the inner wall; and a plunger sliding along the inner wall of along a longitudinal axis of the syringe, the plunger including a plunger head and an operating rod, connected to the plunger head, including, on its outer surface, at least one first rack arranged longitudinally along the operating rod, the first rack including protruding teeth. The first stop and the protruding teeth are also shaped and constituted so as to prevent the plunger from lowering again due to pressure on the operating rod, unless the first rack is disengaged by rotating the plunger within the syringe body around the longitudinal axis so that the first rack faces the first blank surface of the inner wall of the syringe body.

10 Claims, 3 Drawing Sheets

(52) U.S. Cl.
CPC ............ *A61M 2005/31508* (2013.01); *A61M 2202/0014* (2013.01); *A61M 2202/08* (2013.01); *A61M 2205/3341* (2013.01)

(56) References Cited

U.S. PATENT DOCUMENTS

| | | | | |
|---|---|---|---|---|
| 3,938,505 A * | 2/1976 | Jamshidi | ............ | A61B 10/0283 600/566 |
| 4,011,868 A * | 3/1977 | Friend | ................ | A61M 5/31511 604/194 |
| 4,370,987 A * | 2/1983 | Bazell | ................. | A61B 5/1433 600/573 |
| 4,677,980 A * | 7/1987 | Reilly | ................... | A61M 5/007 128/DIG. 1 |
| 4,826,483 A * | 5/1989 | Molnar, IV | ......... | A61M 5/5013 604/110 |
| 4,906,231 A * | 3/1990 | Young | ................ | A61M 5/5013 604/110 |
| 4,925,449 A * | 5/1990 | Saez | ..................... | A61M 5/315 222/386 |
| 5,047,015 A * | 9/1991 | Foote | ................ | A61M 25/1018 604/224 |
| 5,085,638 A * | 2/1992 | Farbstein | .............. | A61M 5/322 128/919 |
| 5,090,962 A * | 2/1992 | Landry, Jr. | ......... | A61M 5/31511 604/110 |
| 5,181,909 A * | 1/1993 | McFarlane | ............ | A61M 5/315 604/191 |
| 5,215,536 A * | 6/1993 | Lampropoulos | ...... | A61M 5/315 604/187 |
| 5,246,011 A * | 9/1993 | Caillouette | ........ | A61B 10/0283 600/566 |
| 5,328,476 A * | 7/1994 | Bidwell | .............. | A61M 5/5013 604/110 |
| 5,453,093 A * | 9/1995 | Haining | ............. | A61M 5/31511 604/110 |
| 5,637,092 A * | 6/1997 | Shaw | .................. | A61M 5/3232 604/110 |
| 5,713,914 A * | 2/1998 | Lee | ..................... | A61M 1/0009 604/321 |
| 5,858,000 A * | 1/1999 | Novacek | ................... | A61L 2/28 604/110 |
| 5,928,202 A * | 7/1999 | Linnebjerg | ......... | A61M 5/31511 604/218 |
| 6,120,479 A * | 9/2000 | Campbell | ........... | A61M 5/5013 604/110 |
| 6,171,286 B1 * | 1/2001 | Gross | .................... | A61M 5/315 604/218 |
| 6,663,593 B2 * | 12/2003 | Ito | ....................... | A61M 5/5066 604/110 |
| 6,773,416 B1 * | 8/2004 | Hsu | ....................... | A61M 5/322 604/110 |
| 7,513,901 B2 * | 4/2009 | Scifert | ............... | A61B 17/8816 606/92 |
| 7,682,345 B2 * | 3/2010 | Savage | ................. | A61M 5/007 604/151 |
| 8,034,024 B2 * | 10/2011 | Rodd | .................... | A61M 5/322 604/110 |
| 8,038,656 B2 * | 10/2011 | Lloyd | ............... | A61M 5/31515 604/218 |
| 8,191,457 B2 * | 6/2012 | Kanner | ............. | A61M 25/1018 604/100.02 |
| 8,974,424 B2 * | 3/2015 | Soma | .................... | A61M 5/315 604/187 |
| 2003/0032928 A1 * | 2/2003 | Sudo | ..................... | A61M 5/315 604/225 |
| 2004/0122345 A1 * | 6/2004 | Muller | .................... | A61M 1/30 604/6.14 |
| 2005/0177107 A1 * | 8/2005 | Dugmore | ............. | A61M 5/322 604/110 |
| 2006/0217670 A1 * | 9/2006 | Cecchi | .................... | A61M 5/19 604/209 |
| 2006/0224144 A1 * | 10/2006 | Lee | ..................... | A61M 1/0009 604/542 |
| 2009/0301480 A1 * | 12/2009 | Elsakka | ............ | A61M 25/0068 128/202.16 |
| 2010/0030074 A1 * | 2/2010 | Imai | .................. | A61B 5/31501 600/432 |
| 2011/0009829 A1 * | 1/2011 | Kosinski | ............ | A61M 5/31511 604/218 |
| 2011/0087173 A1 * | 4/2011 | Sibbitt, Jr. | ......... | A61B 10/0233 604/207 |
| 2012/0316466 A1 * | 12/2012 | Crawford | ......... | A61B 5/150236 600/576 |
| 2013/0098942 A1 * | 4/2013 | Greter | ................... | A61J 1/2096 222/136 |
| 2013/0178425 A1 * | 7/2013 | Higgins | ................. | A61K 35/15 514/16.8 |
| 2014/0231335 A1 * | 8/2014 | Kim | .................... | A61M 1/3693 210/335 |
| 2014/0274650 A1 * | 9/2014 | Ellsworth | ............... | A61L 27/24 494/37 |

\* cited by examiner

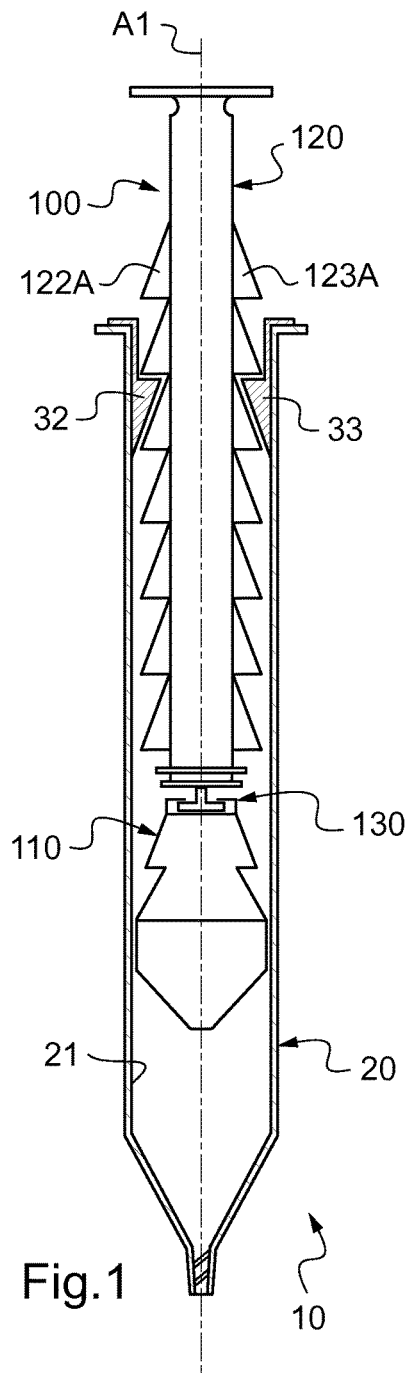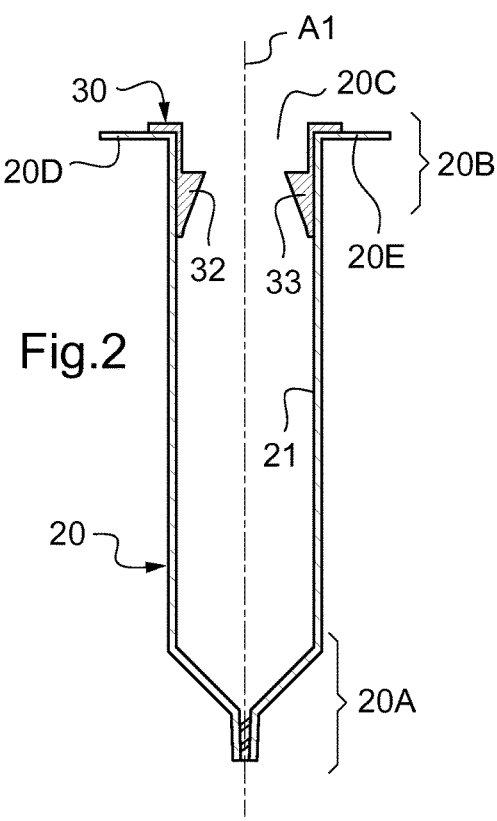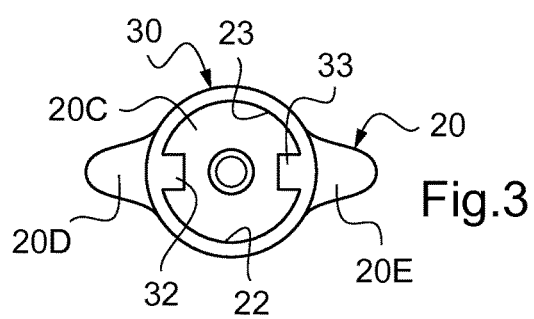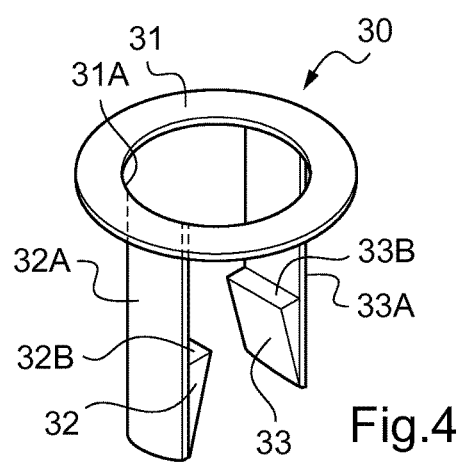

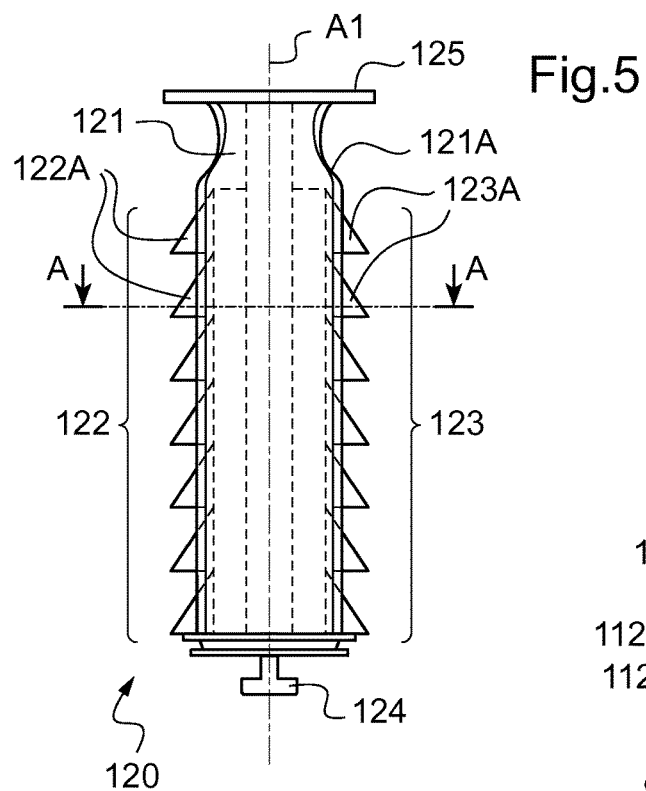
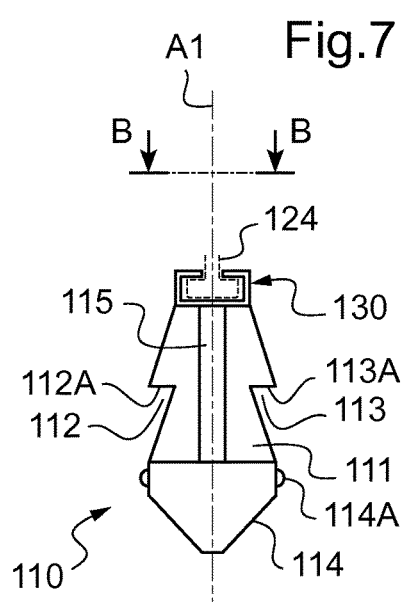
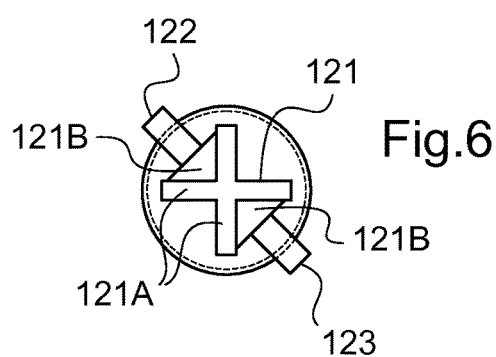
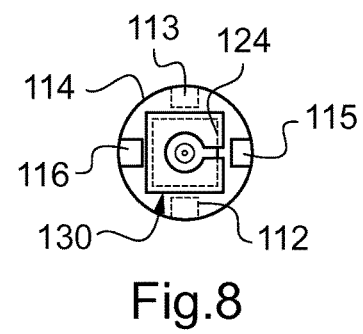
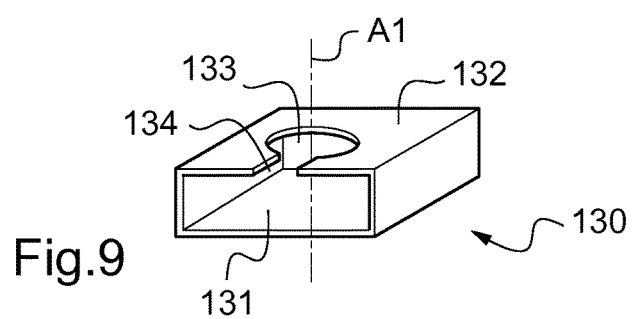

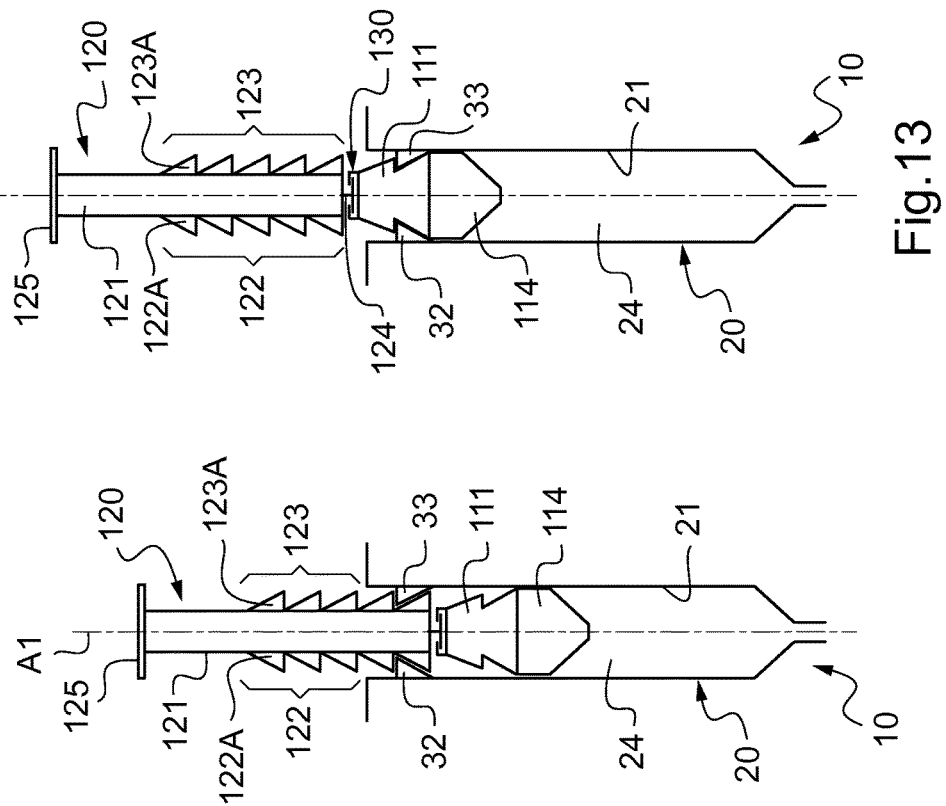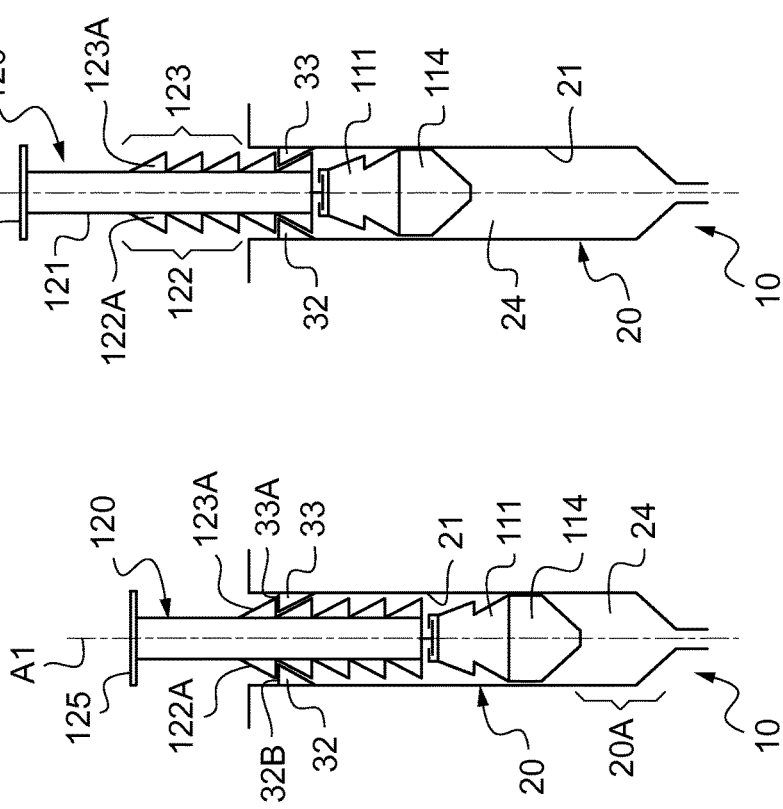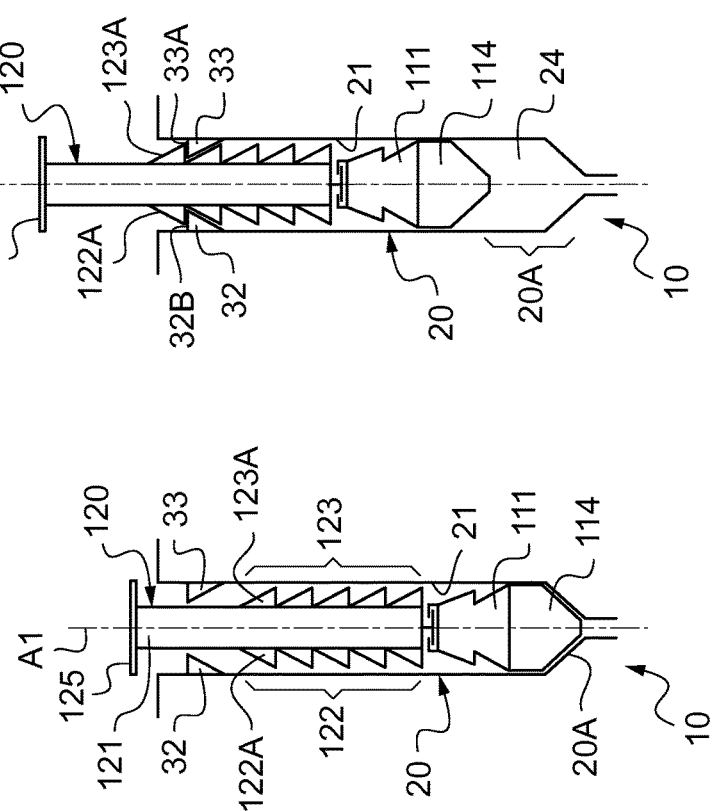

SYRINGE WITH RATCHETING OPERATING ROD AND LOCKABLE PLUNGER HEAD

BACKGROUND OF THE INVENTION

The invention relates to a syringe, and more particularly a syringe for medical applications.

The invention also relates to a syringe that can be used for operations of human adipose tissue liposuction.

DESCRIPTION OF THE RELATED ART

The syringes have been used in medicine, either for sampling operations (blood, tissues, etc. . . . ) or for injection purposes (vaccines, tissues, etc. . . . ).

The syringes are used in particular in plastic surgery in techniques of adipose tissue sampling and reinjection, for example to fill losses of sub-cutaneous substance of a patient. Different techniques of adipose tissue sampling are used today, for example excision or liposuction, the latter being able to be practiced by means of a mechanical suction system or performed manually by means of a syringe.

The latter technique using a syringe as a suction means has been widely engineered, developed and codified by S. R. Coleman, in order to perform a reinjection (graft) of adipose tissue which is lasting (see in particular the article "Hand rejuvenation with structural fat grafting" in Plastic and Reconstructive Surgery, Vol. 110, No. 7, pp. 1731-1744, December 2002 or the article "Structural Fat Grafting: more than a permanent filler" in Plastic and Reconstructive Surgery, Vol. 118, No. 3S, pp. 108S-120S, September 2006).

According to this technique, it is recommended to perform a sampling of adipose tissue on a patient in such a manner to traumatize the less possible the fat cells sampled. For that purpose, it is required to control accurately the vacuum exerted by the syringe on the adipose tissues so that this vacuum is neither too great nor too brutal.

In practice, the surgeon using this technique samples a first volume of adipose tissue with the syringe, and, with the syringe still in the body of the patient at the sampling site, creates a vacuum in the syringe by pulling the plunger in the body of the syringe. The surgeon then waits for the pressures in the syringe and the body of the patient, at the sampling site, to balance each other, thereby removing the vacuum inside the syringe. The surgeon can then sample a second volume of tissue, and wait, and repeat these operations as many times as necessary, until sampling the required quantity of adipose tissue.

Besides, it has been suggested that, if the vacuum applied by the syringe on the adipose tissue, during the upward movement of the syringe plunger in the syringe body, is too high, then the quality of the sampling is lower, which compromises the success of the operations following the liposuction, in particular the survival at mean and long term of the adipose tissue after reinjection of the latter in the sampled patient.

Hence, it has been shown (cf. MD Thesis of M. Ould Ali Djaffar, entitled "*Facteurs mécaniques influençant la qualité des transplants adipocytaires*", delivered by the University of Aix-Marseille in 2010) that the vacuum created by the syringe should remain lower than 0.4 atmosphere (atm) in absolute value, which corresponds for example to a vacuum volume of about 2 cubic centimeter (cc).

The document U.S. Pat. No. 5,047,015 teaches a medical syringe with a plunger provided with a thread on its outer part and a disengagement mechanism allowing to operate the plunger according to two modes. In the first mode, when the mechanism is not activated, the thread of the plunger is engaged and cooperates with another thread present on the inner part of the syringe body, such that the plunger can slide in the syringe body by rotation of the plunger in the syringe body. In the second mode, when the mechanism is activated, the thread of the plunger is disengaged from the other thread, such that the plunger can slide freely in the syringe body.

The document U.S. Pat. No. 5,215,536 describes a medical syringe having a locking system allowing to hold the plunger of a syringe in the syringe body, but to squeeze the syringe body to release the plunger, the latter being then able to slide freely in the syringe body.

The document GB 958636 teaches a syringe intended to deliver a calibrated dose of a substance, this syringe comprising a syringe body having an axis and a spring held in the syringe body, which exhibits elasticity in a plane perpendicular to the axis of the syringe body, a plunger comprising a cruciform operating rod with four arms at 90° relative to each other and stops arranged on the axial faces of the adjacent arms of the cross of the operating rod.

The stops are distributed along the axial faces of the arms of the operating rod so that the stops on the faces of the two arms located in a same plane are aligned between each other and longitudinally offset relative to the stops of the two other arms at 90°.

The stops are adapted to allow, in cooperation with the spring, an upward movement, and a downward movement, "tooth by tooth", of the plunger along the syringe body.

However, the syringe disclosed in the document GB 958636 does not allow the full disengagement of the stops by a simple rotational movement of the plunger in the syringe body, the stops being always in cooperation with the spring.

Moreover, the use of a syringe according to the prior art does not allow to accurately control the sampling volume, and hence the vacuum exerted on the tissue, during the liposuction operation.

Indeed, despite the graduations often present on the outer wall of the syringe body, it is difficult for a surgeon during the sampling operation to control accurately this sampling volume so as not to exceed the limit value of vacuum indicated hereinabove.

In addition, a surgeon using a syringe according to the prior art must always keep his thumb on the syringe body so as to hold the plunger in position in the syringe body during the pressure balance step described hereinabove. A manual liposuction using a syringe of the prior art is hence a laborious operation, because it is the thumb of the surgeon that, over the whole duration of the intervention, exerts the force for holding the plunger. This induces tiredness that may lead to gesture imprecisions of the surgeon or to handling errors. Moreover, when it becomes painful for the thumb, a risk exists of "renunciation" by the surgeon, who will tend to increase the vacuum exerted each time, so as to shorten the intervention.

SUMMARY OF THE INVENTION

To remedy the above-mentioned drawback of the prior art, the present invention proposes a syringe allowing to control the vacuum applied by the syringe during the upward movement of the plunger and to hold without effort the plunger in its position inside the syringe body.

For that purpose, the invention relates to a syringe including:
  a syringe body extending along a longitudinal axis from a lower end to an upper end, the lower end of the syringe body allowing the fixation of a needle or a cannula and the upper end of the syringe body having an upper opening allowing the introduction of a plunger into the syringe body, the syringe body having an inner wall and including at least one first stop located along the inner wall of the syringe body near the upper opening, the first stop being adapted to leave at least one first blank surface on the inner wall of the syringe body, and a plunger sliding along the inner wall of the syringe body along the longitudinal axis, the plunger comprising a plunger head and an operating rod connected to the upper end of the plunger head, the upper end of the plunger head being directed towards the upper opening of the syringe body, the operating rod of the plunger including, on its outer surface, at least one first rack arranged longitudinally along the operating rod, the first rack comprising protruding teeth, the first stop and the protruding teeth being shaped and constituted so as, during the upward movement of the plunger in the syringe body from a low position where the plunger head is near the lower end of the syringe body to a high position where the plunger head is near the upper end of the syringe body, when the first stop and the first rack are opposite to each other, to allow a tooth-by-tooth upward movement of the plunger along the syringe body, the syringe being characterized in that:

the first stop and the protruding teeth are also shaped and constituted so as to prevent any downward movement of the plunger under the effect of a push on the operating rod, but to disengage the first rack by rotation of the plunger in the syringe body about the longitudinal axis to bring the first rack opposite the first blank surface of the inner wall of the syringe body.

Hence, the syringe according to the invention allows to perform operations of adipose tissue sampling by liposuction, with accurate control of the plunger position in the syringe and hence of the sampled volume of tissue thanks to the stops and the protruding teeth, and hence to make sure that the vacuum applied by the syringe is lower than the recommended limit. Therefore, the surgeon does not risk to increase or reduce the sampling volume, and hence the vacuum exerted on the adipose tissues.

Moreover, the protruding teeth and the stops cooperate so as to hold the plunger in its last position, preventing it to move downwards.

By preventing the plunger to move downwards in the syringe body under the effect of a simple push, the syringe according to the invention allows to free the thumb of the surgeon that operates, because the thumb no longer needs to exert a force for holding the plunger in the syringe body. Hence, the thumb is less tired and the gestures of the surgeon are more accurate.

On the other hand, this allows to avoid just-sampled adipose tissue to be reinjected by mistake. Indeed, the syringe according to the invention is not adapted for injections but for suctions.

According to the invention, it is required to disengage the first rack by rotation of the plunger and to bring voluntarily the first rack opposite the blank surfaces if it is desired that the plunger moves downwards.

Moreover, when required, the overpressure created by the downward movement of the plunger has to be the lowest possible so as to traumatize the less possible the fat cells sampled.

Finally, the syringe according to the invention, when placed in a centrifuge after the sampling, prevents a downward movement of the plunger in the syringe body under the effect of the centrifugal force, hence avoiding a degradation of the fat cells sampled.

Besides, other advantageous and non-limitative characteristics of the syringe according to the invention are the following:

the syringe body includes a second stop similar to the first stop, and located along the inner wall of the syringe body, near the upper opening, so that the first and the second stops form between each other a first and a second blank surfaces on the inner wall of the syringe body, and the operating rod includes on its outer surface a second rack similar to the first rack, and arranged longitudinally along the operating rod, so that, when the first rack is opposite the first stop, the second rack is opposite the second stop;

the first and second stops are substantially diametrically opposed to each other, and the first and second racks are also substantially diametrically opposed to each other.

Hence, the syringe according to the invention that has at least two stops, preferably diametrically opposed to each other, allows to limit the transverse movements of the plunger inside the syringe body and makes it easier the manipulation thereof during the liposuction operation. Moreover, as the disengagement of the two racks must be simultaneous, the downward movement by mistake of the plunger in the syringe body is made more difficult.

Other advantageous and non-limitative characteristics of the syringe according to the invention are the following:

the plunger head includes a terminal part facing the lower end of the syringe body, the terminal part being such that it prevents any full disengagement of the plunger from the syringe thanks to a locking by the stop(s), and a base, connected to the terminal part comprising at its periphery at least one first notch and at least one first longitudinal groove, the first notch and the first longitudinal groove of the base being shaped and constituted so as to allow the upward movement and the holding of the plunger in the high position when the first notch is opposite the first stop, and to prevent any downward movement of the plunger along the syringe body, but to disengage the plunger head by rotation of the plunger in the syringe body about the longitudinal axis to bring the first longitudinal groove opposite the first stop;

the base comprises at its periphery a second notch similar to the first notch, and a second longitudinal groove similar to the first longitudinal groove, arranged in such a manner that, when the first longitudinal groove is opposite the first stop, the second longitudinal groove is opposite the second stop;

the first and second longitudinal grooves are substantially diametrically opposed to each other;

the operating rod is detachable from the plunger head;

the plunger head includes a receiving recess integral with the base so that, when the plunger is in the high position, the receiving recess is outside the syringe body, and the plunger operating rod includes at one of its ends an element for connection to the plunger head, the connection element having a shape that is complementary of that of the receiving recess of the piston head, so that, when the plunger is in the high position, the connection element can be engaged into or disengaged from the receiving recess and that, when the connection element is engaged into the receiving recess, the operation rod and the plunger head are translationally integral with each other along the longitudinal axis and rotationally integral with each other about the longitudinal axis;

the receiving recess comprises an open lateral face and an upper face having a central opening substantially positioned along the longitudinal axis of the syringe, so that the connection element is engaged into or disengaged from the receiving recess by being slid through the open lateral face, the central opening allowing the passage of the operating rod.

The syringe according to the invention is particularly well adapted to the use of this syringe in a centrifuge, after the sampling operation.

Indeed, once the sampling ended and the syringed removed from the patient body, it is sometimes required to separate by centrifugation the different cells constituting the adipose tissue sampled. At this stage, the syringe plunger is generally in its high position, so that the whole syringe has a maximal size. However, the space available in a centrifuge is often limited, so that the detachment of the operating rod from the piston head allows to reduce the total size of the syringe to place the latter in the centrifuge.

Besides, according to the invention, the piston head may be held at the high position, even after the operating rod has been detached from the plunger head. Hence, during the centrifugation, there is no risk that the plunger moves again into the syringe body down to the low position, nor that the plunger is fully disengaged from the syringe body, which would be extremely damaging for the sampled tissues.

BRIEF DESCRIPTION OF THE DRAWING FIGURES

A particular embodiment of the invention will be described hereinafter, with reference to the appended drawings in which:

FIG. 1 is an overall view of a syringe according to an embodiment of the invention;

FIG. 2 is a longitudinal sectional view of the body of a syringe according to the embodiment of FIG. 1;

FIG. 3 is a top view of the body of a syringe according to the embodiment of FIG. 1;

FIG. 4 is a perspective view of a ring comprising two stops opposite to each other;

FIG. 5 is a longitudinal sectional view of an operating rod of a syringe plunger according to the embodiment of the invention of FIG. 1;

FIG. 6 is a transverse sectional view (according to the direction A-A of FIG. 5) of the plunger operating rod such as shown in FIG. 5;

FIG. 7 is a longitudinal sectional view of a syringe plunger head according to the embodiment of the invention of FIG. 1;

FIG. 8 is a transverse sectional view (according to the direction B-B of FIG. 7) of the plunger head as shown in FIG. 7;

FIG. 9 is a perspective view of a receiving recess according to the embodiment of the invention of FIG. 1;

FIG. 10 is a sectional view of a syringe according to the embodiment of FIG. 1, when the plunger is in the low position;

FIG. 11 is a sectional view of a syringe according to the embodiment of FIG. 1, when the plunger is in an intermediate position;

FIG. 12 is a sectional view of a syringe according to the embodiment of FIG. 1, when the plunger is in the high position;

FIG. 13 is a sectional view of a syringe according to the embodiment of FIG. 1, when the plunger head is locked by the first and second stops.

DETAILED DESCRIPTION OF THE INVENTION

As a preamble, let's precise that, in the following disclosure, the terms "high" or "upper" and "low" or "lower" will be used in relation to the syringe, the lower side being the side fixed to the needle or the cannula and the upper side being the side from which protrudes the syringe plunger. Likewise, it will be considered that the syringe extends along a substantially vertical direction.

FIG. 1 shows an overall view of a syringe 10 according to a particular embodiment of the invention, this syringe including a syringe body 20.

As shown in FIG. 2, the syringe body 20 has in its lower part an inner wall 21.

The syringe body 20 comprises a lower end 20A serving for the fixation of a needle or a cannula. This lower end 20A has herein a truncated shape. The syringe body 20 also comprises an upper end 20B having a circular opening 20C and two flat areas 20D, 20E. This circular opening 20C allows the introduction of the plunger 100 as described in details hereinafter.

The syringe body 20 is substantially of revolution about a longitudinal axis A1, so that the intermediate part of the syringe body, located between the lower end 20A and the upper end 20B is cylindrical.

The syringe body 20 has herein a total height of the order of 80 millimeters and an inner diameter of the order of 15 millimeters, hence defining a volume of about 14 milliliters.

Furthermore, the syringe body 20 has herein a thickness of about 1 millimeter.

As a variant, the syringe body may for example have a total height going up to 150 millimeters and a lower diameter of 25 millimeters, hence defining a volume that can go up to about 75 milliliters.

According to this embodiment, the syringe body 20 is made of polypropylene by a moulding process.

As a variant, the syringe body may be made of another plastic material, as for example polycarbonate, metal or glass.

The syringe body 20 is preferably transparent. This allows the surgeon, who performs a sampling with a syringe 10 according to the embodiment of the invention, to see inside the syringe 10 the quantity, and eventually the nature, of the sampled tissues.

The syringe body 20 is provided, near its upper end 20B, with a ring-shape piece 30.

As shown in FIG. 4, this ring 30 includes a flat annular part 31 as well as two arms 32A, 33A extending downwards from the lower face of the flat annular part 31, from the lower edge 31A thereof. According to the embodiment of the invention, the two arms 32A, 33A are herein diametrically opposed to each other.

The arm 32A includes a first stop 32 and the arm 33A includes a second stop 33, the first and second stops 32, 33 thus being diametrically opposed to each other. The first and second stops 32, 33 have a triangular prism shape, whose tip is directed downwards, and protrude towards each other.

The first and second stops 32, 33 have bearing surfaces 32B and 33B, which are substantially horizontal and rectangular in shape.

The first and second stops 32, 33 have herein a height comprised between 2 and 15 millimeters and the bearing surfaces 32B, 33B have a width comprised between 1 and 10 millimeters and a depth comprised between 0.5 and 7 millimeters.

According to this embodiment, the ring 30 is made of polypropylene, by a moulding process. Preferentially, the ring 30 is consisted of a material whose colour is different from that of the syringe body 20 so as to allow the distinction between them and to rapidly make sure of the presence of the ring 30 in the syringe body 20.

As a variant, the ring may be made of another plastic material, as for example polycarbonate, or also metal.

According to the embodiment of the invention described herein, the ring 30 is inserted and fixed in the syringe body 20 by nesting of the ring 30 at the circular opening 20C, the material of the ring 30 being flexible enough so as to be elastically deformed and introduced by force in the syringe body 20.

As shown in FIGS. 2 and 3, the flat annular part 31 then bears on the two flat areas 20D, 20E and on the circular edge of the upper end 20B of the syringe body 20. Likewise, the dimensions of the ring 30 are adjusted so that the distance between the two arms 32A, 33A is very slightly higher than the inner diameter of the syringe body 20, the arms 32A, 33A then bear on the inner wall 21 of the syringe body 20, so that the nesting of the ring 30 of the syringe body 20 or the rotation thereof inside the syringe body 20 about the longitudinal axis A1 requires a significant effort.

So arranged, the ring 30 and the syringe body 20 leave between the first and second opposite stops 32, 33, a first and a second blank surfaces 22, 23 on the inner wall 21 of the syringe body 20. The first and the second stops 32, 33 being herein substantially diametrically opposite to each other, the first and the second blank surfaces 22, 23 are hence also substantially diametrically opposite to each other.

As shown in FIG. 1, the syringe 10 according to this embodiment of the invention also includes a plunger 100, the plunger 100 comprising a plunger head 110, an operating rod 120 and a receiving recess 130.

The total length of the operating rod 120 is herein of about 100 millimeters.

The operating rod 120 includes an outer surface 121 whose precise structure is described in FIGS. 5 and 6.

This outer surface 121 comprises a cross pin 121A with four arms, orthogonal two by two, and two support elements 121B arranged in two opposite intervals, formed between two consecutive arms of the cross pin 121A.

The two support elements 121B extend longitudinally along the operating rod 120. One of the support elements 121B includes a first rack 122 arranged longitudinally along the operating rod 120, the first rack 122 comprising protruding teeth 122A.

The other support element 121B includes a second rack 123 similar to the first rack 122 comprising protruding teeth 123A and arranged longitudinally along the operating rod 120.

These protruding teeth 122A, 123A protrude outwards from the outer surface 121 of the operating rod 121. As shown in FIG. 6, the protruding teeth 122A, 123A are more precisely positioned on two opposite arms of the cross-shaped outer surface 121.

The protruding teeth 122A, 123A have a triangular prism shape and are oriented in the opposite direction relative to the stops 32, 33. They are made of a flexible plastic material.

According to this embodiment, the first and second racks 122, 123 are herein diametrically opposed to each other and each comprise seven protruding teeth 122A, 123A, preferably equidistant to each other, the protruding teeth 123A of the second rack 123 being diametrically opposed to the protruding teeth 122A of the first rack 122.

The operating rod 120 includes in its lower part a connection element 124 including a parallelepipedal part on which is placed a cylindrical part. The operation of this connection element 124 will be described in more details hereinafter, in particular in the description of the receiving recess 130.

Moreover, the operating rod 120 includes in its upper part a flatten area 125 allowing the plunger 100 to be slid in the syringe body 20, either downwards by pushing on the flatten area 125, or upwards by pulling on the flatten area 125.

The plunger 100 also includes a plunger head 110 such as described in FIGS. 7 and 8.

The plunger head 110 includes at its lower end a terminal part 114 that is of revolution about the longitudinal axis A1. The terminal part 114 is a conventional terminal part of a syringe plunger head. It has a cylindrical shape in its upper part to be adapted to the cylindrical shape of the intermediate part of the syringe body 20 and a conical shape in its lower part so as to be adapted to the truncated shape of the lower end 20A of the syringe body 20.

The terminal part 114 includes an O-ring 114A at its periphery so that the plunger 100 slides sealingly along the inner wall 21 of the syringe body 20, hence preventing any leakage of the substance sampled or injected with the syringe 10.

The terminal part 114 of the plunger head 110 is made of polypropylene.

As a variant, the terminal part may be made of polyethylene, polytetrafluoroethylene (PTFE), or fluorinated ethylene propylene (FEP).

The terminal part 114 is generally black so as to facilitate the reading of the sampled or injected volume on the graduations present on the syringe body 20.

As shown in FIG. 7, on the upper face of the terminal part 114 of the plunger head 110 is fixed a base 111. This base 111 is of truncated shape.

The truncated shape that is linked to the terminal part 114 has a diameter comprised between 14 and 25 millimeters according to the syringe model considered. In its upper part, the base 111 has a truncated section having a diameter comprised between 12 and 23 millimeters.

The base 111 includes a first notch 112 and a second notch 113, in recess, each formed at its periphery, such that the first and second notches 112, 113 are diametrically opposed to each other, as can be seen in FIG. 8. The first and second notches 112, 113 are located at about half the height of the base 111, separating the base into an upper part and a lower part.

The first and second notches 112, 113 are triangular in shape so as to define a first and a second planar faces 112A, 113A, which are substantially horizontal and directed downwards.

In the particular embodiment described in FIGS. 7 and 8, the first and second notches 112, 113 have a depth comprised between 0.5 and 7 millimeters and a width comprised between 1 and 10 millimeters.

These dimensions are substantially identical to the dimensions of the first and second stops 32, 33, such that the shape of the first and second stops 32, 33 is substantially complementary to that of the first and second notches 112, 113.

The base 111 also includes a first groove 115 and a second groove 116, rectilinear, formed at its periphery, over the whole height of the base 111.

As shown in FIG. 8, the first and second rectilinear grooves 115, 116 are diametrically opposed to each other and arranged on the periphery of the base 111 such that, on the one hand, the first rectilinear groove 115 is located between the first notch 112 and the second notch 113, and forms with each of them an angle of 90 degrees, and that, on the other hand, the second rectilinear groove 116 is located between the second notch 113 and the first notch 112, and also forms with each of them an angle of 90 degrees.

As a variant, the first and second notches 112, 113 and the first and second rectilinear grooves 115, 116 cannot be diametrically opposed to each other. Likewise, the first and second notches 112, 113 and the first and second rectilinear grooves 115, 116 can be separated by an angle different from 90 degrees.

The first and second rectilinear grooves 115, 116 have a width comprised between 1 and 11 millimeters and a depth comprised between 0.5 and 8 millimeters. Their width is slightly higher than the width of the first and second stops 32, 33.

The base 111 is made of a flexible plastic material of the polyethylene type.

As a variant, the base may for example be made of polypropylene, polycarbonate, polytetrafluoroethylene or fluorinated ethylene propylene.

The plunger head 110 finally includes at its upper end a receiving recess 130 made by machining.

As an alternative, the receiving recess is fixed on the upper part of the base 111, by adhesive bonding.

As illustrated in FIG. 9, this receiving recess 130 is parallelepiped in shape. It hence defines a receiving volume. Herein, the receiving recess 130 has a square base: it has an edge comprised between 10 and 30 millimeters and a height comprised between 5 and 15 millimeters according to the size of the syringe considered.

The receiving recess 130 comprises an open lateral face 131 and an upper face 132 perpendicular to the longitudinal axis A1.

This upper face 132 has at its centre a circular opening 133 centred about the longitudinal axis A1 and a straight groove 134 extending from the open lateral face 131 to the central opening 133.

The receiving recess 130 is hence dimensioned so as to receive the connection element 124 of the operating rod 120.

The operating rod 120 is herein detachable from the plunger head 110 thanks to the removable link between the connection element 124 and the receiving recess 130.

Indeed, the connection element 124 is engaged with or disengaged from the receiving recess 130 by being slid through the open lateral face 131, the parallelepipedal part of the connection element 124 being nested into or separated from the receiving recess 130, the straight groove 134 and the central opening 133 allowing the passage of the cylindrical part of the connection element 124 during the nesting or the separation of the parallelepipedal part of the connection element 124.

Once nested into the receiving recess 130, the connection element 124 can no longer rotate in the receiving recess 130. In this case, the connection element 124 being attached to the connection rod 120, on the one hand, and the receiving recess 130 being attached to the plunger head 110, on the other hand, the operating rod 120 is rotationally integral with the plunger head 110 about the longitudinal axis A1.

Likewise, the operating rod 120 is translationally integral with the plunger head 110 along the longitudinal axis A1.

When the operating rod 120 is connected to the plunger head 110 at its upper end, the notch 112 and the rack 122 on the one hand, and the notch 113 and the rack 123 on the other hand, are herein aligned with each other.

The operation of the syringe 10 according to the particular embodiment described hereinabove will now be described with respect to FIGS. 10 to 13.

We consider herein a tissue sampling operation performed by an operator, where the initial state of the syringe 10 is that shown in FIG. 10.

In this initial position, the plunger 100 is in its low position with respect to the syringe body 20, i.e. the terminal part 114 of the plunger head 110 presses on the lower end 20A of the syringe body 20, the respective shapes thereof being complementary of each other.

The operating rod 120 is in part inside the syringe body 20, its upper end and in particular the flatten area 125 being located outside the syringe body, which allows the operator manipulating the syringe 10 to make the plunger 100 slide along the inner wall 21 of the syringe body 20 along the longitudinal axis A1, by pulling on the operating rod 120 at the level of the flatten area 125.

In the situation illustrated in FIG. 10, the first rack 122 is aligned with the first stop 32, and the second rack 123 is aligned with the second stop 33. The width of the operating rod 120 at the outer surface 121 including the first and second racks 122, 123 is lower than the inner diameter of the syringe body 20 such that the protruding teeth 122A, 123A does not rub against the inner wall 21 of the syringe body 20, which hence limit the pulling force that the operator has to exert on the operating rod 120 to make the plunger 100 slide in the syringe body 20 along the longitudinal axis A1.

Starting from the situation illustrated in FIG. 10, the operator hence pulls on the operating rod 120 to begin sampling tissue. The plunger 10 then slides in the syringe body 20 along the longitudinal axis A1. The first and second racks 122, 123, and more particularly the first two protruding teeth 122A, 123A directed towards the upper end of the operating rod 120 move inside the syringe body 20 up to arrive opposite the first and second stops 32, 33.

The distance between the first two protruding teeth 122A, 123A being higher than the distance between the first and second stops 32, 33, the operator cannot continue to easily pull on the operating rod 120.

The operator must then exert an additional force so as to move the first two protruding teeth 122A, 123A past the first and second stops 32, 33, thanks to the elastic deformation of the first two protruding teeth 122A, 123A.

Once having moved past the first and second stops 32, 33, the first two protruding teeth 122A, 123A bear on the bearing surfaces 32B, 33B of the first and second stops 32, 33 preventing any downward move of the plunger 100 under the effect of a push on the operating rod 120.

In this configuration shown in FIG. 11, the terminal part 114 of the plunger head 110 does no longer bear on the lower end 20A of the syringe body 20 but is moved upwards inside the syringe body 20, hence defining a first sampling volume 24.

The position of the first two protruding teeth 122A, 123A are determined so that this first sampling volume 24 corresponds to such a volume that the corresponding vacuum exerted on the sampled tissue is lower than a threshold value.

Here, the syringe body 20 having a total volume of 10 milliliters, the first sampling volume 24 is equal to 2 cubic centimeters, limiting the vacuum exerted to value of 0.4 atmosphere (in absolute value).

By repeating several times the preceding step, the operator moves the plunger 100 upwards, "tooth by tooth", in the syringe body 20, the additional volume sampled, and hence the vacuum exerted on the sampled tissues, being always the same due to the constant distance determined between the protruding teeth 122A, 123A.

FIG. 12 shows an intermediate situation where the plunger 100 is located between the above-described low position and the high position described in more details hereinafter. In this configuration, the first and second stops 32, 33 and the first and second racks 122, 123 are opposite to each other. Two protruding teeth 122A, 123A bearing on the two bearing surfaces 32B, 33B of the stops 32, 33, the plunger 100 cannot move downwards in the syringe body 20.

So as to disengage the first and second racks 122, 123, the operator bring the first rack 122, respectively the second rack 123, opposite the first blank surface 22, respectively the second blank surface 23, of the inner wall 21 of the syringe body 20 by rotation of the plunger 100 in the syringe body 20 about the longitudinal axis A1.

Hence, the width of the outer surface 121 of the operating rod 120 being lower that the distance between the first and the second stops 32, 33, the plunger 100 can slide without hindrance along the inner wall 21 of the syringe body 20.

The operator may then either bring the plunger 10 down to its low position, such as shown in FIG. 10, or lock again the plunger 100 in the intermediate position by reengaging the first and second racks 122, 123 into the first and second stops 32, 33 by rotation of the operating rod 120.

If, starting from the situation shown in FIG. 12, the operator continues to move the plunger 100 upwards, tooth by tooth, by making the plunger slide along the syringe body 20, the movement will end in the passage of all the protruding teeth 122A, 123A of the first and second rack 122, 123 as shown in FIG. 13. Then, only the plunger head 110 remains inside the syringe body 20, and in particular the receiving recess 130, which then forbids any detachment of the operating rod 120 from the plunger head 110 by sliding of the connection element 124 outside the receiving recess 130.

By continuing to exert a pulling force on the operating rod 120, the operator brings the upper part of the base 111 between the first and second stops 32, 33, the base 111 being deformed thanks to its elasticity, as the protruding teeth 122A, 123A. The first and second stops 32, 33 are then opposite the first and second notches 112, 113, and the first and second planar faces 112A, 113A of the first and second notches 112, 113 bear on the first and second bearing surfaces 32B, 33B of the first and second stops 32, 33.

As hereinabove, the passage of the first base part 111 increases the sampling volume by such a value that the corresponding vacuum exerted on the sampled tissues is lower than the above-defined threshold value, and preferably similar to the moving tooth by tooth.

When the first and second notches 112, 113 are opposite the first and second bearing surfaces 32B, 33B of the first and second stops 32, 33, the plunger 100 is held in the high position and cannot move downwards along the syringe body 20.

So as to disengage the plunger head 110, the operator brings the first longitudinal groove 115 opposite the first stop 32 by rotation of the plunger 100 in the syringe body 20 by means of the operating rod 120. The second stop 33 and the second longitudinal groove 116 being diametrically opposed to the first stop 32 and to the first longitudinal groove 115, respectively, the second stop 33 and the second longitudinal groove 116 are then also opposite to each other.

Moreover, the first and second racks 122, 123 being aligned with the first and second notches 112, 113, they are located above and in the alignment with the first and second blank surfaces 22, 23.

Hence, the operator can then slide the plunger 100 downwards inside the syringe body 20 by exerting a pushing force on the operating rod 120.

Besides, as shown in FIG. 13, when the plunger 100 is in the high position, the terminal part 114 prevents any full disengagement of the plunger 100 from the syringe body 20 thanks to the locking of the plunger head 110 by the first and second stops 32, 33.

Indeed, the terminal part 114 being made of a rigid material, the operator cannot fully disengage the plunger 100 from the syringe body 20, but to exert voluntarily a very high pulling force on the operating rod 120. This avoids that involuntary errors of manipulation fully disengage the plunger head 110 from the syringe body 20 and possibly compromise the quality of the sampling.

Furthermore, the longitudinal position of the first and second notches 112, 113 on the base 111 is such that, in the high position shown in FIG. 13, the upper end of the plunger end, and more particularly the receiving recess 130, protrudes enough from the upper end 20B of the syringe body 20 to allow the disengagement of the connection element 124 by its sliding out of the receiving recess 130.

The operating rod 120 may then be detached from the piston head 110, which reduces the total length of the syringe 10 when the plunger head 110 is in the high position and hence facilitating the manipulation of the syringe 10.

The invention claimed is:
1. A syringe (10) including:
a syringe body (20) extending along a longitudinal axis (A1) from a lower end (20A) to an upper end (20B), the lower end (20A) of the syringe body (20) allowing the fixation of a needle or a cannula and the upper end (20B) of the syringe body (20) having an upper opening (20C) allowing the introduction of a plunger into the syringe body (20), the syringe body (20) having an inner wall (21) and including at least one first stop (32) located along the inner wall (21) of the syringe body (20) near the upper opening (20C), the first stop (32) being adapted to leave at least one first blank surface (22) on the inner wall (21) of the syringe body (20), and
a plunger (100) sliding along the inner wall (21) of the syringe body (20) along the longitudinal axis (A1), the plunger (100) comprising a plunger head (110) and an operating rod (120) connected to the upper end (110B) of the plunger head (110), the upper end (110B) of the plunger head (110) being directed towards the upper opening (20C) of the syringe body (20), the operating rod (120) of the plunger (100) including, on its outer surface (121), at least one first rack (122) arranged longitudinally along the operating rod (120), the first rack (122) comprising protruding teeth (122A),
the first stop (32) and the protruding teeth (122A) being shaped and constituted so as, during the upward movement of the plunger (100) in the syringe body (20) from a low position where the plunger head (110) is near the lower end (20A) of the syringe body (20) to a high position where the plunger head (110) is near the upper end (20B) of the syringe body (20), when the first stop (32) and the first rack (122) are opposite to each other, to allow a tooth-by-tooth upward movement of the plunger (100) along the syringe body (20), the syringe (10) being characterized in that the first stop (32) and the protruding teeth (122A) are also shaped and constituted so as to prevent any downward movement of the plunger (100) under the effect of a push on the operating rod (120), but to disengage the first rack (122) by rotation of the plunger (100) in the syringe body (20) about the longitudinal axis (A1) to bring the first rack (122) opposite the first blank surface (22) of the inner wall (21) of the syringe body (20), wherein the plunger head (110) includes:
- a terminal part (114) facing the lower end (20A) of the syringe body (20), the terminal part (114) being such that it prevents any full disengagement of the plunger (100) from the syringe body (20) thanks to a locking by the stop(s), and
- a base (111), connected to the terminal part (114), comprising at its periphery at least one first notch (112) and at least one first longitudinal groove (115), the first notch (112) and the first longitudinal groove (115) of the base (111) being shaped and constituted so as to allow the upward movement and the holding of the plunger (100) in the high position when the first notch (112) is opposite the first stop (32), and to prevent any downward movement of the plunger (100) along the syringe body (20), but to disengage the plunger head (110) by rotation of the plunger (100) in the syringe body (20) about the longitudinal axis (A1) to bring the first longitudinal groove (115) opposite the first stop (32).

2. The syringe (10) according to claim 1, wherein:
- the syringe body (20) includes a second stop (33) similar to the first stop (32), and located along the inner wall (21) of the syringe body (20), near the upper opening (20C), so that the first and the second stops (32, 33) form between each other a first and a second blank surfaces (22, 23) on the inner wall (21) of the syringe body (20), and wherein
- the operating rod (120) includes on its outer surface (121) a second rack (123) similar to the first rack (122), and arranged longitudinally along the operating rod (120), so that, when the first rack (122) is opposite the first stop (32), the second rack (123) is opposite the second stop (33).

3. The syringe (10) according to claim 2, wherein:
- the first and second stops (32, 33) are diametrically opposed to each other, and
- the first and second racks (122, 123) are also diametrically opposed.

4. The syringe (10) according to claim 1, wherein the base (111) comprises at its periphery:
- a second notch (113) similar to the first notch (112), and
- a second longitudinal groove (116) similar to the first longitudinal groove (115), arranged in such a manner that, when the first longitudinal groove (115) is opposite the first stop (32), the second longitudinal groove (116) is opposite the second stop (33).

5. The syringe (10) according to claim 4, wherein the first and second longitudinal grooves (115, 116) are diametrically opposed to each other.

6. The syringe (10) according to claim 1, wherein the operating rod (120) of the plunger is detachable from the plunger head (110).

7. The syringe (10) according to claim 6, wherein:
the plunger head (110) includes a receiving recess (130) integral with the base (111) so that, when the plunger (100) is in the high position, the receiving recess (130) is outside the syringe body (20), and wherein
the operating rod (120) includes at one of its ends an element (124) for connection to the plunger head (110), the connection element (124) having a shape that is complementary of that of the receiving recess (130) of the piston head (110), so that, when the plunger (100) is in the high position, the connection element (124) can be engaged into or disengaged from the receiving recess (130) and that, when the connection element (124) is engaged into the receiving recess (130), the operation rod (120) and the plunger head (110) are translationally integral with each other along the longitudinal axis (A1) and rotationally integral with each other about the longitudinal axis (A1).

8. The syringe (10) according to claim 7, wherein the receiving recess (130) comprises an open lateral face (131) and an upper face (132) having a central opening (133) substantially positioned along the longitudinal axis (A1) of the syringe (10), so that the connection element (124) is engaged into or disengaged from the receiving recess (130) by being slid through the open lateral face (131), the central opening (133) allowing the passage of the operating rod (120).

9. The syringe (10) according to claim 4, wherein the operating rod (120) of the plunger is detachable from the plunger head (110).

10. The syringe (10) according to claim 5, wherein the operating rod (120) of the plunger is detachable from the plunger head (110).

* * * * *